United States Patent [19]

Ferrario

[11] Patent Number: 5,508,499

[45] Date of Patent: Apr. 16, 1996

[54] METHOD AND APPARATUS FOR THE UNIVOCAL AND PERMANENT CONNECTION OF CONTAINERS FOR MEDICAL USE TO A GIVEN PATIENT

[75] Inventor: Angelo Ferrario, Busto Arsizio, Italy

[73] Assignee: Healtech S.A., Balzers, Liechtenstein

[21] Appl. No.: 962,577

[22] PCT Filed: Jun. 21, 1991

[86] PCT No.: PCT/EP91/01167

§ 371 Date: Dec. 30, 1992

§ 102(e) Date: Dec. 30, 1992

[87] PCT Pub. No.: WO92/01268

PCT Pub. Date: Jan. 23, 1992

[30] Foreign Application Priority Data

Jul. 11, 1990 [IT] Italy .................................... 20907/90

[51] Int. Cl.⁶ ............................ G06F 15/20; G06K 7/10; G06K 19/06
[52] U.S. Cl. ........................ 235/375; 235/456; 235/494; 209/3.3; 209/524; 209/583
[58] Field of Search ..................... 235/375, 456, 235/494, 487; 209/3.3, 524, 583

[56] References Cited

U.S. PATENT DOCUMENTS

| | | | |
|---|---|---|---|
| 4,362,928 | 12/1982 | Sheldon | 235/494 |
| 4,457,420 | 7/1984 | Ducloux | 198/369 |
| 4,487,322 | 12/1984 | Juvinall | 209/526 |
| 4,614,531 | 9/1986 | Bishop et al. | 65/158 |
| 4,638,144 | 1/1987 | Latta, Jr. | 219/121 LH |
| 4,857,713 | 8/1989 | Brown | 235/375 |
| 4,857,716 | 8/1989 | Gombrich | 235/375 X |
| 4,877,948 | 10/1989 | Krueger | 235/456 |
| 4,930,263 | 6/1990 | Rando | 235/487 |
| 4,990,792 | 2/1991 | Frei | 250/566 |
| 5,150,795 | 9/1992 | Nakayama et al. | 209/3.3 |
| 5,153,416 | 10/1992 | Neeley | 235/375 |

FOREIGN PATENT DOCUMENTS 0317325  5/1989  European Pat. Off. .

*Primary Examiner*—Donald T. Hajec
*Assistant Examiner*—Jeffrey R. Filipek
*Attorney, Agent, or Firm*—Sixbey, Friedman, Leedom & Ferguson; Gerald J. Ferguson, Jr.; Evan R. Smith

[57] ABSTRACT

The apparatus comprises a device for the transfer (13) of containers (12) which takes containers (12) from a magazine for containers (11) to convey them in succession to a delivery station (16) passing through means for labelling (14) and means for checking the labels (25) controlled by a control and data acquisition system (2) so as to univocally label each single container with the data related to a corresponding single patient to a corresponding single sanitary event.

1 Claim, 2 Drawing Sheets

METHOD AND APPARATUS FOR THE UNIVOCAL AND PERMANENT CONNECTION OF CONTAINERS FOR MEDICAL USE TO A GIVEN PATIENT

BACKGROUND OF THE INVENTION

The present invention relates to a method and apparatus for the univocal and permanent connection of containers for medial use to a given patient.

In a clinical investigation process it is possible to distinguish between a pre-analytical step, an analytical step and a post-analytical step.

The pre-analytical step is the step which precedes the analysis and is constituted by the processing of the prescription made by the 'base doctor' or by the 'specialist doctor' (with all the flow of related data among the different bodies which have a say in the matter, from the administrative bodies to the technical ones, to end with the party directly affected), by the taking of the sample, by its identification, by the subsequent handling towards and within the laboratory's operational centres, by the corresponding handling operations (other than the analytical ones).

The analytical step is the step in which the material is analysed in its components and the post-analytical step is the step in which the results of the analyses are collected and printed in a final report which is handed to the patient and/or to the doctor.

The strong growth in demand for laboratory work over the past twenty years has involved great technological development with the creation of a wide area of laboratory automation: in particular the analytical step and the post-analytical step have been automated, while scant attention has been paid to the automation of the pre-analytical step.

In current laboratory medicine the processing of raw materials constituted by biological materials (blood, urine, etc.) taken from the same patient, as well as their communication, occurs manually or, under the best of circumstances, semi-automatically and in any case, at all times, with serious prejudice to the correct attribution of the analytical result.

In the case of manual processing the doctor or the nurse who takes the sample manually writes the patient's name (and possibly the requested analyses) on the test tube in which the biological material (blood, urine, etc.) is collected, and on the request for analyses.

Generally speaking, when they enter the laboratory, a number is written on the test tubes belonging to each single patient and on the request for analyses, commonly known as the access number, which, under the best of circumstances, is repeated each time there is a transfer of biological material from the original test tube to other subsidiary test tubes; thus number out to constitute the safety element for the identification of the material along the entire process. In certain cases the access number is then replaced with another number, different from one type of analysis to the next, or from one laboratory section to the other.

The name of the patient is obtained at the time the sample is taken by asking the patient himself (if he is conscious) or by taking it from the bed in which the patient is or from the clinical record (when the patient is unconscious).

The risks of error connected with these operations are obvious: possibility of error in the manual writing on a test tube and/or a request for analysis on the part of a tire operator who, perhaps, has spoken with two patients in succession; possibility of exchanging data from one patient's clinical record and another's name; possibility of exchanging test tubes and/or medical reports related to different patients. In addition, error is intrinsic in the above-mentioned methodology since the systematic exchange of technology and code number, in the different operations of identification of the different steps constituting the analytical process, systematically creates such a possiblity.

In the case of semi-automatic operations, when the patient is admitted, to hospitals or other health organizations equipped with a computer, a certain number of labels is produced containing the name and address of the patient, which are inserted in his clinical record. When it is necessary to execute laboratory analyses, the section staff takes one or more labels, adds the necessary data (say, the analyses requested at that time, the date, etc.) and manually sticks them on to the test tubes into which the biological material will be inserted. As an alternative, labels are produced by the computer when it is necessary to execute laboratory analyses.

It is obvious that, in these cases, such information cannot be ready by machines.

Progress over this system has been attained during the past few years by providing the patient, at admittance, with an identification card with a bar code. Such identification card, generally located in the clinical record or at the patient's bed, or contained in an armlet which cannot be removed from the patient, is read by a suitable reader which transmits the information to a bar code printer capable of duplicating it on adhesive labels, subsequently stuck manually both on to the preprinted forms of requests for analyses and on to the test tubes which will contain the patient's biological materials.

In the laboratory there is in this case available on each test tube and/or corresponding request for analyses information readable by man and/or information readable by means of a suitable device capable of identifying the patient and if necessary the analyses to be executed in an indirect and non-univocal form over time.

Such a semi-automatic identification system, even though it does represent an improvement with respect to the manual system, has some limits.

The paper support requires an adequate size for the test tube, it requires case in handling the test tube and, in addition, the glue with which it adheres to the test tube can penetrate, due to the permeability of the wall, into the test tube thus contaminating its contents.

If the solution with the bar code is adopted, which today represents the most advanced technology, it is also necessary to consider that the space utilized with this type of memorisation is comparatively large so that on the label of an ordinary test tube only one code can be stored with which to access the complete series of the patient's data stored, say, in the central computer, in the peripheral computer or in the clinical record.

Lastly, the operation of manually reading from the test tube or from the armlet can it itself be a source of human error.

All these processes in any case involve a non-obligatory temporal continuity between the time the sample is taken and the preparation of the test tube, so that there is always the risk of exchanging test tubes between two patients.

SUMMARY OF THE INVENTION

EP-A-0317325 discloses a sample analysis and tracking system including a sample collecting station controlled by a computer to sequentially write and read identification data on labels attached to bottles for collecting samples.

This known system however does not give absolute certainty against possible collecting of samples in bottles provided with labels marked with erroneous identification data.

The object of the present invention is that each container utilized in a medical ambit for holding biological samples, drugs o other material relating to a given patient and to a given sanitary event to be univocally and permanently provided with identification data which are to be sufficiently complete, automatically readable by machine and, possibly but not necessarily, by man as well, non-perishable, automatically derived from the patient, suitable for being remaining unaltered during the entire processing cycle with the automatic reproduction of same when necessary (say, to identify secondary test tubes, medical reports, samples placed in cold-storage for future uses, etc.).

In one embodiment of the present invention these objects are attained by a method for the univocal and permanent association of medical containers to be given patient, which provides for the following succession of steps: a) storing patient identification data in at least one computer and on a support connected to the patient; b) when a given sanitary event is required, reading said patient identification data on said support and comparing them with those stored in the computer to receive consent for further processing; c) marking said patient identification data in permanent way on at least one medical container; and d) reading the patient identification data marked on said container and comparing them with those stored in the computer to receive consent for making the marked container available for immediate filling of the container with a sanitary product relating to the patient.

To accomplish this method, the present invention further provides an apparatus for the delivery of medial containers univocally and permanently associated to a given patient, which comprises at least one computer for storing patient identification data, a control station for reading patient identification data on a support connected to the patient and comparing them with those stored in the computer to give consent for further processing, a container magazine, transfer means controlled by the control station to take at least one container from said magazine and to convey it towards a container delivery station through a container processing path, marking means arranged in the processing path and controlled by the control station to mark the patient identification data ion the container in a permanent way, and checking means arranged in said processing path downstream of the marking means and controlled by the control station to read the patient identification data marked on the container and to compare them with those stored in the computer to give consent for sending the marked container to the delivery station.

In this way, directly at the moment of use for a given patient, each single container, such as, say, a test tube for blood tests, a container of drugs and so on, is automatically marked in a permament manner with a safe personal identification code, which has previously been subjected to comparison and consent, has a perennial validity for each single patient if so required, is complete and suitable for remaining unchanged throughout the analysis path right up to the report stage.

So as to ensure the time correspondence between the marking operation of the container and the sanitary event for which it is to be used (say, taking a sample of biological material for which the container itself is to be used, the time at which the drug contained in the container is to be administered) and in any case the control of the time in which marking has occurred, the apparatus according to the invention can be equipped with means for programming over time the "marking" event of the container and/or the latter's release from the wrapper holding it and/or the opening of same with the contents being made available, in any case wit the indication of the time in which the event has taken place.

BRIEF DESCRIPTION OF THE DRAWINGS

The features of the present invention shall be made more evident by the following detailed description of an embodiment illustrated as a non-limiting example in the enclosed drawings, wherein.

DETAILED DESCRIPTION OF THE PREFERRED EMBODIMENTS

Figure 1:
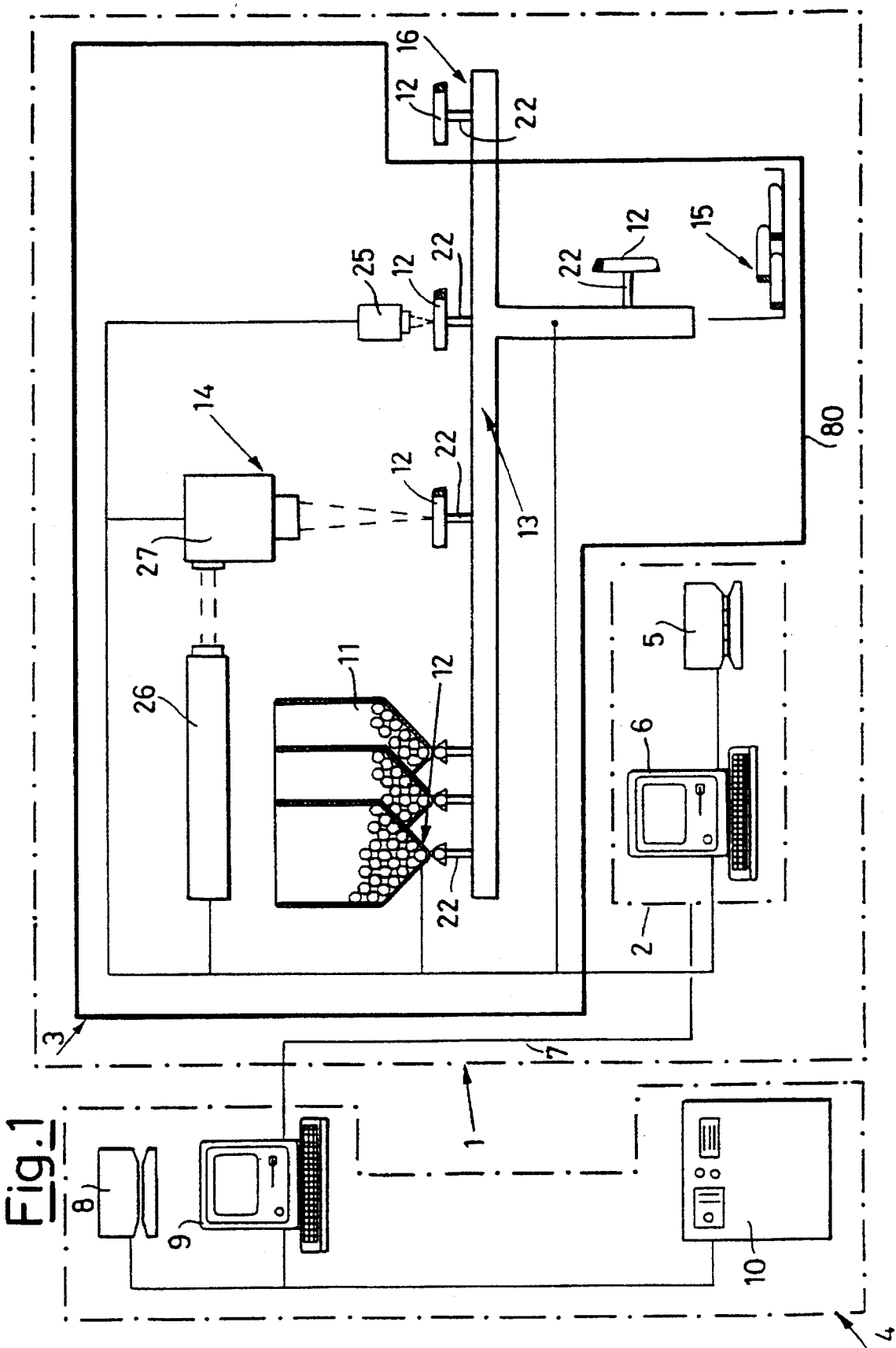
FIG. 1 illustrates diagramatically an apparatus for the accomplishment of the method according to the invention.

There is indicated with 1 in FIG. 1 a station for taking biological samples, which comprises an apparatus 3 for the delivery and marking of test tubes with which there is associated a control and data acquisition station 2.

The control and data acquisition station 2 comprises an identification card reader 5 and a personal-type computer 6 suitable for exchanging information through a line 7 with a remote admittance station 4, if necessary. This consists of an identification card reader 8 connected by means of a line with a personal-type computer 9, for the temporary storage of information read by reader 8 and a central computer 10 of an operational type.

The apparatus 3 comprises a magazine 11, say, constituted by a series of hoppers, three in the figure, which may be operated separately for the delivery of empty test tubes 12 on to supports 22 of a transfer device 13. Downstream from magazine 11 there is a marking station 14, consisting of a laser source 26 and a device 27 for the deviation and concentration of the laster beam, which indelibly marks test tubes 12, if desired also holographically; as an alternative, the marking station 14 can comprises a diamond-tipped tool driven by an electromechanical device, as commonly provided for in the so-called <<Klischograf>>, or a "plasma" tool may also be used. The transfer device 13 then takes the test tubes to a checking device 25, say, a series of capacitative coupling diodes, for verifying the correctness of the markings, and then to a delivery station 16. The apparatus also comprises a rejection station 15 which collects the incorrectly marked test tubes 12. It should be noted that the delivery station 16 is the only position to which the operator has access from the outside of the overall housing 80 of the apparatus 3.

If so desired, the apparatus may also be equipped with means capable of programming over time the operation of the marking station 14 and of the delivery station 16.

Figure 2:
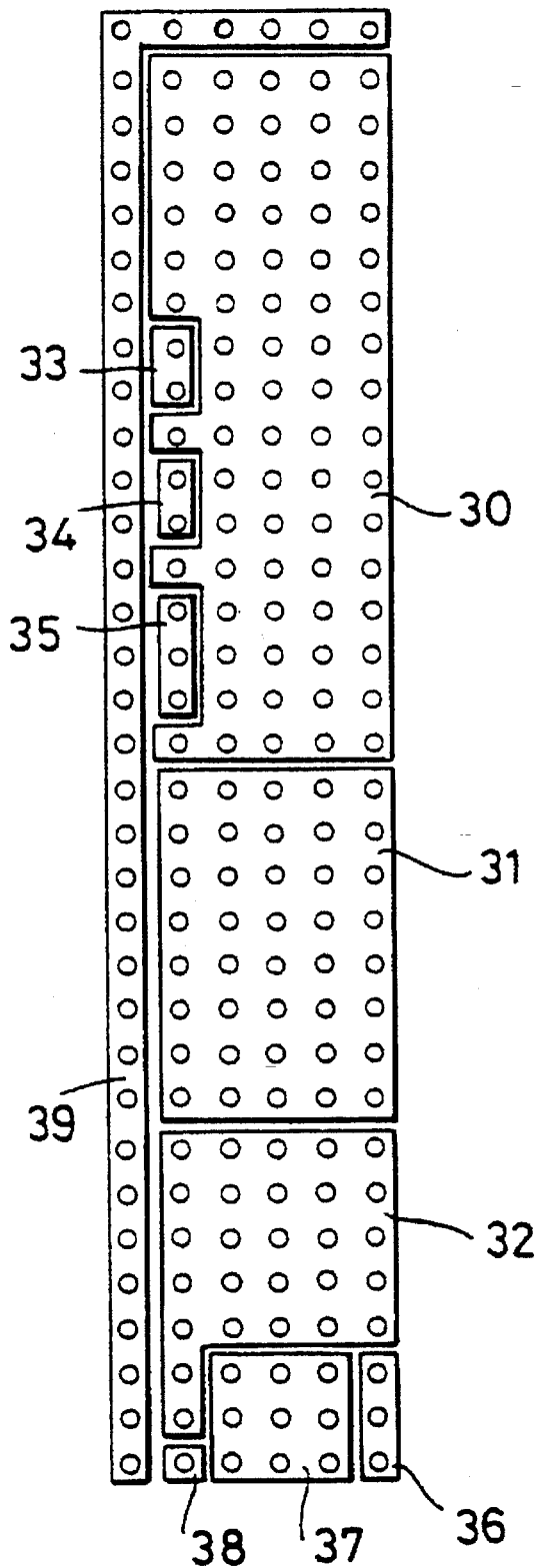
FIG. 2 shows an example of the marking operation of a container by means of the apparatus of FIG. 1.

There is illustrated in FIG. 2 an example of a marking operation which provides for the creation, on the test tube 12, of a 198-bit matrix.

An area 30 of the matrix is reserved for marking the patient's identification code. In the case of a patient having Italian nationality the tax code number may be used, which has nine letters and seven decimal numbers. Each letter may be selected among 26 possibilities and thus coding in a binary code requires 5 bits ($2^5=32$) to take care of all possibilities. For the ten possible decimal numbers 4 bits are necessary ($2^4=16$) to take care of all possibilities. This makes it necessary to use 5×9 bits for the identification of the letters and 4×7 bits for the identification of the numbers for a total of 45+28=73 bits.

An area 32 is reserved for the time coding of the event (taking the sample). The structure of this code has 5 bits for the identification of the ay (from 01 to 31), 4 bits for the indication of the month (from 01 to 12), 7 bits for the last two figures of the year, 5 bits for the hour:00÷23) at which the sample is taken, 6 bits for the minute (00÷59) at which the sample is taken. The time identification of the sample thus involves 27 bits altogether.

A 40-bit area 31 is dedicated to the analytical path so that, for a test tube analytical path having 40 different analyses, all the simple variable class combinations from 1 to 40 are available, in any case chosen among the 40 possible ones.

Areas 33, 34, 35 the first two having two bits, the third having three bits, are dedicated to the coding of the type of sample to be taken, of the level of danger of the test tube and of any possible additional information regarding the patient, respectively.

A three-bit area 36 gives the possiblity of choosing among eight different recipients of the clinical record.

In an area 37 there are available 9 bits left in reserve to cover possible future needs.

An area 38 contains a bit used as a parity check. The check consists in the conventional definition that the sum of '1s' and '0s' can be any number at will, even or odd, and in processing the parity bit so that the defined condition is always verified. During the reading step, the fact that the parity condition is not satisfied constituted an irregularity. The fact that parity is verified can not, obviously, be taken as a definitive proof of correctness, but it is certainly a necessary condition (though it is not sufficient) for the code to be considered correct.

There is also an area 39 containing bits for synchronisation signals, that is, signals dedicated to define the bits' positioning lattice.

It should lastly be noted that, if the patient does not have a tax code (or a similar code such as the American "Social security number"), a temporary code may be assigned to the patient. In this case five bits of area 30 are used to indicate that it is a temporary code, five bits for the indication of the day of birth, four bits for the indication of the month of birth, seven bits for the indication of the year of birth, sixteen bits for the assignment of a numerical code to be assigned to the individual in question so as to differentiate him from all the others who may have been born on the same day. In this case there would be 36 unused bits available.

The operation of the apparatus shown in the drawings is as follows.

Upon admittance, at remote station 4, the patient's identification card is inserted into the identification card reader 8. The information read (or, as an alternative, introduced by means of a keyboard or otherwise obtained, say, by modem or facsimile) are stored in computer 9 and possibly completed with data introduced by means of the keyboard directly into computer 9. The complete data related to the patient is transferred to storage in central computer 10. Such a succession of operations ends with the appointment for taking the sample.

The operation of taking the sample comprises a preliminary step operated by the control and data acquisition unit 2 through computer 6, which verifies the consistency between the data read by reader 5 from the patient's identification card (or introduced by means of the keyboard) and the data corresponding to the patient's reservation made at remote admittance station 4 and stored in central computer 10. According to the number of test tubes to be delivered, computer 6 orders the sequential opening of a corresponding number of hoppers 11. From hoppers 11 the test tubes 12 fall on to supports 22 arranged on transfer device 13, which executes their transfer to the marking station 14. When the individual test tube 12 reaches the marking station 14, the latter, controlled by computer 6, execute the marking of same. Test tube 12 is then transferred to the checking device 25 which reads the identification data on the test tube and, controlled by computer 6, verifies the correctness of the marking and the consistency between the marking of test tube 12 and the patient identification data stored by computer 6. If the operation has a positive outcome, the test tube 12 is transferred to delivery station 16; otherwise it is transferred to rejection station 15.

I claim:

1. Apparatus for the delivery of medical containers univocally and permanently associated with a given patient, comprising at least one computer for storing patient identification data, a control station for reading patient identification data on a support connected to the patient and comparing them with those stored in the computer to give consent for further processing, a container magazine, transfer means controlled by said control station to take at least one container from said magazine and to convey it towards a container delivery station through a container processing path, marking means arranged in said processing path and controlled by said control station to mark said patient identification data ion said container in a permanent way, and checking means arranged in said processing path downstream of said marking means and controlled by said control station to read the patient identification data marked on said container and to compare them with those stored in the computer to give consent for sending the marked container to the delivery station;

characterized in that it further comprises means for programming an activation time for operation of said transfer means, marking means, and checking means, and subsequently automatically activating said transfer means, marking means, and checking means at said activation time.

* * * * *